(12) United States Patent
Bakhirkin et al.

(10) Patent No.: US 10,006,844 B2
(45) Date of Patent: Jun. 26, 2018

(54) FLUID DENSITY METERS AUTO-START BY INJECTION SEED VIBRATION USING FREQUENCY SCANNING METHOD

(71) Applicant: THERMO FISHER SCIENTIFIC INC., Sugar Land, TX (US)

(72) Inventors: Yury A. Bakhirkin, Houston, TX (US); Alexander Joseph Esin, Sugar Land, TX (US); Yanzhong Li, Missouri City, TX (US)

(73) Assignee: Thermo Fisher Scientific Inc., Sugar Land, TX (US)

( * ) Notice: Subject to any disclaimer, the term of this patent is extended or adjusted under 35 U.S.C. 154(b) by 107 days.

(21) Appl. No.: 14/958,147

(22) Filed: Dec. 3, 2015

(65) Prior Publication Data

US 2016/0161386 A1   Jun. 9, 2016

Related U.S. Application Data

(60) Provisional application No. 62/087,672, filed on Dec. 4, 2014.

(51) Int. Cl.
*G01N 9/00* (2006.01)
*G01N 9/34* (2006.01)

(52) U.S. Cl.
CPC ............... *G01N 9/002* (2013.01); *G01N 9/34* (2013.01)

(58) Field of Classification Search
CPC ............ G01N 9/00; G01N 9/002; G01N 9/24; G01N 9/36
USPC ................................................ 73/32 A, 32 R
See application file for complete search history.

(56) References Cited

U.S. PATENT DOCUMENTS

| | | | |
|---|---|---|---|
| 2008/0224783 A1* | 9/2008 | Tanaka | A61B 17/320068 331/4 |
| 2009/0084178 A1* | 4/2009 | Sinha | G01N 11/167 73/32 A |
| 2014/0331766 A1* | 11/2014 | Kramer | G01N 29/022 73/32 A |

* cited by examiner

*Primary Examiner* — Benjamin Schmitt
(74) *Attorney, Agent, or Firm* — Edgardo J. Mantilla; William R. McCarthy, III

(57) ABSTRACT

A method of initiating a fluid density measurement includes generating a prime resonance of a test fixture by a startup circuit. The method of initiating a fluid density measurement includes closing a feedback loop in response to generating the prime resonance. The method of initiating a fluid density measurement includes maintaining the prime resonance by closing the feedback loop.

14 Claims, 9 Drawing Sheets

FLUID DENSITY METERS AUTO-START BY INJECTION SEED VIBRATION USING FREQUENCY SCANNING METHOD

RELATED APPLICATIONS

The present application claims priority from U.S. Provisional Patent Application Ser. No. 62/087,672, titled "FLUID DENSITY METERS AUTO-START BY INJECTION SEED VIBRATION USING FREQUENCY SCANNING METHOD", filed Dec. 4, 2014, which is hereby incorporated by reference herein in its entirety for all purposes.

FIELD OF THE DISCLOSURE

The present invention relates generally to fluid property measurement.

BACKGROUND

In general, fluid properties relate to intrinsic properties of a fluid. For example, the density of a fluid is the mass per unit of volume of the fluid. It is sometimes necessary to measure the properties of fluids. The method of measuring each property of a fluid varies depending on the fluid property.

SUMMARY

In one aspect, a method of initiating a fluid density measurement according to one or more embodiments may include generating a prime resonance vibration of a test fixture by a startup circuit; closing a feedback loop in response to generating the prime resonance vibration; and maintaining the prime resonance vibration frequency by closing the feedback loop.

In one aspect, a fluid density meter according to one or more embodiments may include a startup circuit that may determine a prime resonance frequency of a test fixture and a switch that may close a feedback loop in response to the startup circuit determining the prime resonance frequency. The feedback loop may maintain a resonance vibration frequency of the test fixture.

In one aspect, a fluid density meter according to one or more embodiments may include a frequency scanning circuit and a test fixture that generates a resonance frequency in response to a plurality of vibrations. The test fixture may include a vibration source that generates the plurality of vibrations in response to a stimulation voltage; an interior region that holds a test fluid and transmits the plurality of vibrations to the test fluid; and a pickup circuit that converts the resonance frequency to an output voltage based on the resonance frequency. The fluid density meter may include a startup trigger that activates a frequency scanning circuit in response to a fluid test initiation and a prime resonance frequency detecting circuit that detects a prime resonance frequency based on the output voltage and sends a prime resonance frequency detected signal to the frequency scanning circuit in response to detecting the prime resonance vibration.

In one aspect, a method of initiating a fluid density measurement according to one or more embodiments may include applying a first stimulation voltage to a test fixture; generating a plurality of vibrations based on the first stimulation voltage; sweeping a frequency of the first stimulation voltage over a range; modifying the plurality of vibrations based on sweeping the frequency of the first stimulation voltage; generating a resonance frequency and a prime resonance vibration of the test fixture based on the modified plurality of vibrations; determining the prime resonance frequency based on a first magnitude of an output voltage associated with the prime resonance vibration and a second magnitude of an output voltage associated with the resonance vibration; and maintaining the prime resonance vibration by applying a feedback voltage, based on the detected prime resonance frequency, to the test fixture.

BRIEF DESCRIPTION OF DRAWINGS

Certain embodiments of the invention will be described with reference to the accompanying drawings. However, the accompanying drawings illustrate only certain aspects or implementations of the invention by way of example and are not meant to limit the scope of the claims.

DETAILED DESCRIPTION

Specific embodiments will now be described with reference to the accompanying figures. In the following description, numerous details are set forth as examples of the disclosure. It will be understood by those skilled in the art that one or more embodiments of the present invention may be practiced without these specific details and that numerous variations or modifications may be possible without departing from the scope of the invention. Certain details known to those of ordinary skill in the art are omitted to avoid obscuring the description.

Embodiments disclosed herein are directed toward fluid density meters. A fluid density meter may be capable of measuring the density of a fluid. A fluid density meter may be used, for example, to measure the density of a fluid flowing along a fluid line. The fluid density meter may, for example, be inserted in-line with or as a stub along the fluid line to receive a sample of the fluid. When a fluid density measurement is initiated, the fluid density meter may interrogate the fluid sample by generating vibrations that interact with the sample fluid. Based on the interaction of the vibrations with the sample fluid, the fluid density meter determines a density of the fluid.

Figure 1:
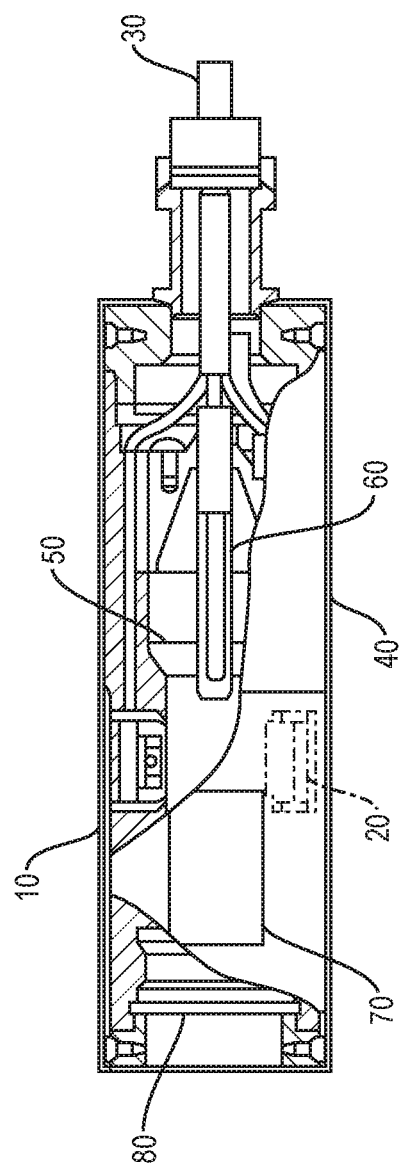
FIG. 1 shows an example of a test fixture.

A fluid density meter may include a test fixture that receives a test fluid and a circuit that applies a voltage to the test fixture. FIG. 1 shows an example of a Thermo Fischer Scientific Sarasota® test fixture. The example test fixture may include a coil assembly (driving) (10), a coil assembly (pickup) (20), a signal cable (30), a housing (40), a vibrating spool (50), a temperature sensing element such as an RTD (60), an exterior marking (70), and a spool holder (80). The test fixture may convert the applied voltage to vibrations that extend throughout the test fixture and the test fluid within the test fixture. The amplitude of vibrations created by the test fixture corresponds to the frequency of the applied voltage. In the example shown in FIG. 1, the coil assembly (driving) (10) converts an applied voltage received by the signal cable (30) to vibrations.

Converting the applied voltage to vibrations may excite a resonance frequency vibration of the test fixture. A resonance of the test fixture is a mechanical vibration at a resonance frequency that occurs at a discrete frequency. For example, a test fixture may have a resonance vibration that occurs at a frequency of 2 kHz. In other words, the test fixture may resonate if vibrations at a frequency of 2 kHz are applied to the test fixture.

The test fixture may support multiple resonance frequencies. Each resonance vibration has an associated resonance frequency. For example, a test fixture may support a first resonance frequency at 1 kHz and a second resonance frequency at 2 kHz. In other words, the test fixture may resonate if vibrations at a frequency of 1 kHz or 2 kHz are applied to the test fixture.

The associated frequency of each resonance of the multiple resonance frequencies may depend on the density of the test fluid. For example, if the test fluid has a density of 1 g/cm$^3$, e.g. water, the frequency of a first resonance may be 1.5 kHz. As another example, if the test fluid has a density of 1.11 g/cm$^3$, e.g. ethylene glycol, the frequency of the first resonance may be 1.3 kHz. Thus, the associated frequency of each resonance of the multiple resonance frequencies of the test fixture may depend on the density of the test fluid.

When a resonance frequency is excited in the test fixture, the test fixture may output a voltage, corresponding to the resonance frequency, to the circuit. When a resonance frequency is not excited in the test fixture, the test fixture may output a voltage having a much lower amplitude to the circuit that may not maintain self-sustained oscillations. In the example shown in FIG. 1, the coil assembly (pickup) (20) converts vibrations to an output voltage when the test fixture resonates. When the test fixture shown in FIG. 1 resonates, the vibrations generated by the coil assembly (driving) (10) transmit to the coil assembly (pickup) (20). Conversely, when the test fixture shown in FIG. 1 does not resonate, the vibrations generated by the coil assembly (driving) (10) have a much lower amplitude compared to when the test fixture resonates. When the vibrations having much lower amplitude transmit to the coil assembly (pickup) (20) a much lower output voltage is generated. Thus, the test fixture shown in FIG. 1 selectively generates an output voltage having a large magnitude when the test fixture resonates.

The circuit may receive the output voltage and determine a fluid density based on the frequency of the received output voltage. As discussed above, the associated frequency of each resonance of the multiple resonance frequencies of the test fixture depends on the density of the test fluid. The dependence of the associated frequency of each resonance of the multiple resonance frequencies of the test fixture on the density of the test fluid is known in the art and thus measuring a frequency of a resonance of the test fixture may be used to determine a density of the test fluid.

For example, when a test fixture is empty, the test fixture may have a first resonance frequency of 2 kHz and a second resonance frequency of 4.2 kHz. When a test fluid is in the test fixture, the test fixture may have a first resonance frequency of 1.8 kHz and a second resonance frequency of 3.8 kHz. Thus, measuring a resonance frequency of the test fixture may be used to determine a density of the test fluid based on the difference in frequency between a resonance frequency of the test fixture with the test fluid and the resonance frequency of the test fixture without the test fluid. In other words, the test fixture may measure the density of the test fluid based on the dispersion of the fixture resonant frequency with density.

However, simply measuring a resonance frequency, as discussed above, may not be sufficient to determine the density of the fluid. As discussed above, applying a voltage to the test fixture at a predetermined frequency may generate a resonance frequency of the test fixture, but it is not possible to know which resonance frequency of the multiple resonance frequencies has been generated. For example, when a second test fluid is in the test fixture of the previous example, the second resonance frequency may be 1.8 kHz. As discussed above, when the first test fluid is in the test fixture, the test fixture may have a first resonance frequency of 1.8 kHz. Thus, a measured resonance frequency of the test fixture is not uniquely associated with a fluid density. In other words, if a voltage having a frequency of 1.8 kHz is applied to the test fixture and the test fixture resonates, it is not possible to know if the test fixture includes the first test fluid or the second test fluid because it is not known if the resonance is a first resonance or a second resonance.

In view of the above, embodiments of the disclosure relate to a circuit and method of generating a predetermined resonance frequency in the test fixture of the multiple resonance frequencies supported by the test fixture. By generating a predetermined resonance frequency, the ambiguity in the relationship between a measured resonance frequency of the test fixture and the density of the test fluid may be removed. Thus, by generating a predetermined resonance frequency vibration in the test fixture, the predetermined resonance frequency corresponds directly to a fluid density which prevents errors in determining the density of the test fluid due to the ambiguity in the relationship between a measured frequency and the density of the test fluid.

In one or more embodiments of the disclosure, the fluid density meter may include a startup circuit that generates a predetermined resonance frequency, or prime resonance frequency, of a test fixture and detects the prime resonance frequency once generated. The startup circuit may send a signal to a switch indicating that a prime resonance frequency has been detected in response to detecting the prime resonance frequency. In response to receiving the detected prime resonance frequency, the switch may close a feedback loop including the test fixture. Closing the feedback loop may disconnect the startup circuit from the test fixture. The closed feedback loop may maintain the prime resonance frequency vibration in the test fixture. A fluid density measurement as known in the art may be performed based on the prime resonance frequency maintained in the test fixture. For example, when the prime resonance frequency vibration is maintained, the resonant frequency may be measured and subsequently used to calculate a fluid density as is known in the art.

As discussed above, the test fixture may be configured to support a prime resonance frequency and a second resonance frequency. By maintaining the prime resonance frequency while performing the resonant frequency measurement, the fluid density meter according to one or more embodiments of the disclosure may accurately determine the density of the fluid.

In one or more embodiments of the disclosure, the test fixture may be configured to receive a time varying voltage and generate vibrations based on the time varying voltage. In one or more embodiments of the disclosure, the frequency of the generated vibrations is proportional to the frequency of the time varying voltage, e.g. a time varying voltage at 1 kHz may cause vibrations at 1 kHz to be generated. In response to the generated vibrations, the test fixture may resonate if the frequency of the vibrations corresponds to a resonant frequency of the test fixture.

In one or more embodiments of the disclosure, the test fixture is an electromechanical resonator that includes a fluid compartment. The electromechanical resonator may support multiple resonance frequencies that change based on the properties of the fluid. When a fluid is in the compartment, each resonance frequency of the multiple resonance frequencies may change based on the density of the fluid. For example, a more dense fluid may shift the resonance frequencies of the test fixture to lower frequencies when compared to the resonant frequencies of the test fixtures loaded with a less dense fluid in the fluid compartment.

The test fixture may output a voltage that is proportional to the magnitude of a resonance frequency vibration. For example, the test fixture may include a piezoelectric source on one side of the test fixture and a piezoelectric receiver on a second side. The piezoelectric source may generate vibrations in response to a time varying voltage. If the frequency of the applied time varying voltage does not correspond to a resonant frequency, the vibrations may not transmit along the length of the test fixture and reach the piezoelectric receiver. Thus, an output voltage may not be generated in response to an applied voltage that does not correspond to a resonance frequency.

If a time varying voltage at a resonant frequency is applied, the vibrations generated by the piezoelectric source may transmit along the length of the resonator and be received by the piezoelectric receiver. In response to the received vibrations, the piezoelectric receiver may generate a voltage that is proportional in magnitude to the magnitude of the received vibrations. The generated voltage in response to the received vibrations may be output.

In one or more embodiments of the disclosure, the fluid density meter may include a sweeping circuit that excites a prime resonance frequency vibration and a second resonance frequency vibration of the multiple resonances of the test fixture. In one or more embodiments of the disclosure, the prime resonance is the lowest order resonance mode of vibration of the test fixture. In one or more embodiments of the disclosure, the second resonance vibration is any resonance frequency mode of vibration other than the lowest order resonance frequency mode of the vibration of the test fixture. The sweeping circuit may supply a time varying voltage to the electromechanical resonator and sweep the frequency of the time varying voltage over a range. By sweeping the frequency of the time varying voltage, the sweeping circuit may sequentially excite resonance frequencies vibrations over a period of time corresponding to the sweep rate of the frequency. As noted above, the test fixture may generate an output voltage corresponding to each resonance. Thus, resonance frequencies may be detected based on the output voltage when the frequency of the time varying voltage applied to the test fixture is swept.

In one or more embodiments of the disclosure, the fluid density meter may include a prime resonance detection circuit. The prime resonance detection circuit may receive an output voltage from the test fixture. As the sweeping circuit sweeps the frequency of the applied voltage, the test fixture may generate an output voltage corresponding to each resonance as described above. The magnitude of the output voltage may be proportional to the order of the resonant mode of the test fixture generated in response to the applied time varying voltage. The prime resonance detecting circuit may identify a prime resonance frequency based on the magnitude of the output voltage.

For example, the test fixture may output a 10 mV signal in response to an applied time varying voltage that is at a frequency that corresponds to a second order. In response to receiving the 10 mV output voltage, the prime resonance detecting circuit may determine that the 10 mV signal does not correspond to a prime resonance frequency. In another example, the test fixture may output a 25 mV signal in response to an applied time varying voltage that is at a second frequency that corresponds to a prime resonance frequency vibration. In response to receiving the 25 mV output voltage, the prime resonance detecting circuit may determine that the 25 mV signal does correspond to a prime resonance frequency. In response to determining that the received voltage corresponds to a prime resonance frequency, the prime resonance detecting circuit may send a signal to the frequency scanning circuit to terminate generating a time varying voltage.

Thus, embodiments of the disclosure may facilitate generation of a prime resonance frequency vibration mode in a test fixture and prevent generation of any other resonant frequency vibration mode.

Figure 2:
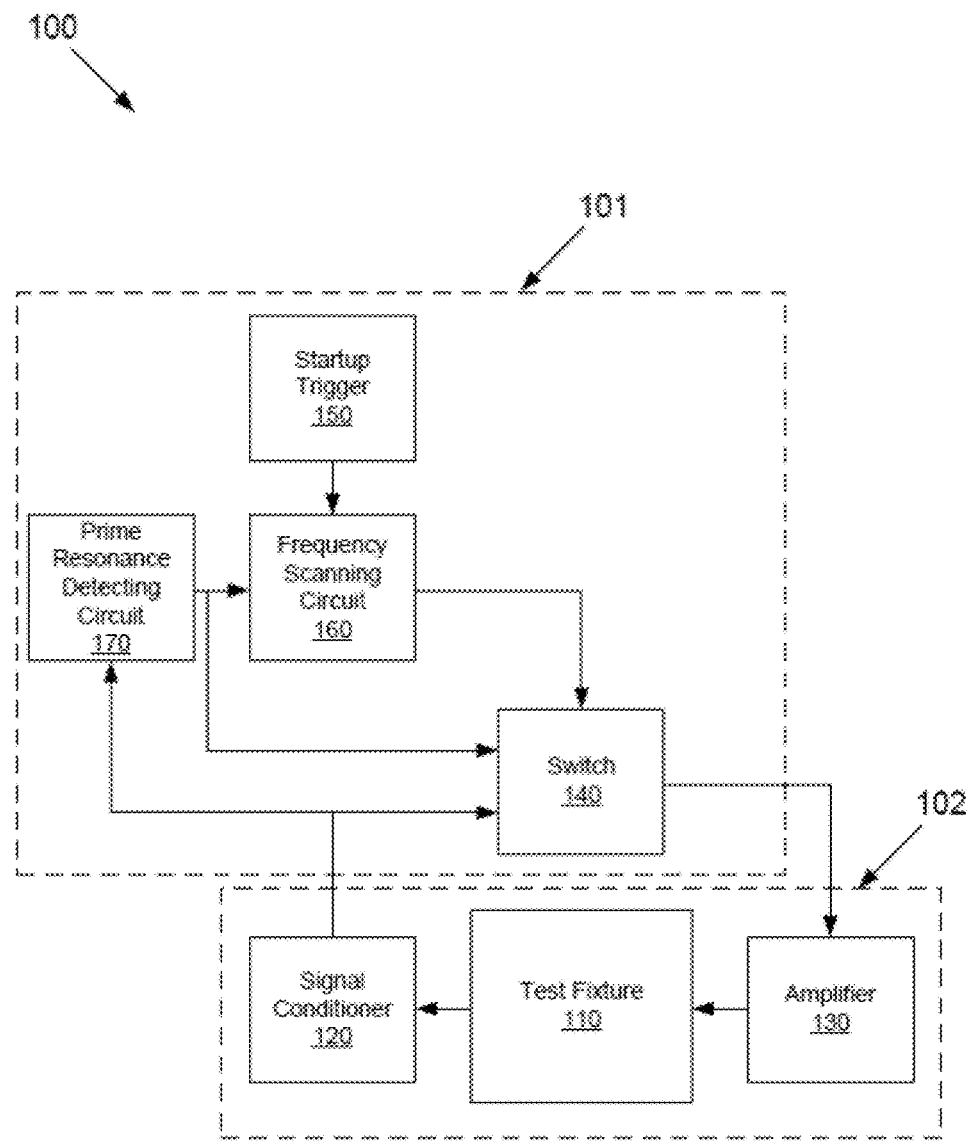
FIG. 2 shows a diagram of a fluid density meter in accordance with one or more embodiments of the disclosure.

FIG. 2 shows a diagram of a fluid density meter (100) according to one or more embodiments of the disclosure. Specifically, FIG. 2 shows a fluid density meter (100) including a startup circuit (101) and a feedback loop (102). Arrows in FIG. 2 indicate the direction of signal or voltage flow. The startup circuit (101) may preferentially select a resonance frequency of a test fixture (110) and the feedback loop (102) may maintain the resonance frequency vibration once the resonance frequency is selected.

The feedback loop (102) includes a test fixture (110), a signal conditioner (120), and an amplifier (130). The feedback loop (102) may maintain an electromechanical resonance vibration between the test fixture (110), the signal conditioner (120), and the amplifier (130). As discussed above, the test fixture (110) may receive a time varying voltage and generate an output voltage if the time varying voltage corresponds to a resonant frequency of the test fixture. While the test fixture (110) has been previously described as containing piezoelectric transmitters and receivers, the test fixture (110) may include any type of transducer as would be known to one of ordinary skill in the art to convert the applied time varying voltage to vibrations and convert vibrations that are transmitted to the receiver to an output voltage. For example, a transmitting magnetic coil and a receiving magnetic coil may also be used in the test fixture. In one or more embodiments, the output voltage may have a magnitude that is substantially lower than the applied voltage. Thus, merely applying the output voltage as the applied voltage to the test fixture may not maintain the resonance frequency vibrations.

The signal conditioner (120) and amplifier (130) may increase the magnitude of the output voltage before applying the output voltage to the test fixture (110) as the applied voltage. In one or more embodiments of the disclosure, the signal conditioner (120) may be an electric circuit. The electric circuit may be implemented as an analog circuit as a printed circuit board and discrete elements as is known in the art. The electric circuit may also be implemented as a digital circuit, such as a microcontroller including instructions stored on a non-transitory computer readable medium. For example, the microcontroller may receive the output voltage from the test fixture and convert the output voltage to digital data by an analog to digital converter according to instructions contained on the non-transitory computer readable medium. The microcontroller may then process the digital data to condition the signal and then output the conditioned signal by a digital to analog converter. In another example, the signal conditioner may be further implemented as a digital signal processing (DSP) unit containing instructions stored on a non-transitory computer readable medium as is known in the art. In one or more embodiments, the signal conditioner (120) may filter, average, or clamp the magnitude of the signal to within a range as is known in the art.

The amplifier (130) may amplify the signal output from the signal conditioner (120) and apply the amplified signal to the test fixture (110) as the applied voltage. Thus, the output signal from the test fixture (110) may be conditioned by the signal conditioner (120), amplified by the amplifier (130), and applied to the test fixture (110) as the applied voltage. The aforementioned steps may maintain a resonance frequency vibration of the test fixture (110).

The startup circuit (101) may include a switch (140), startup trigger (150), frequency scanning circuit (160), and prime resonance detecting circuit (170). As noted above, the startup circuit (101) may preferentially select a prime resonance frequency which may then be maintained by the feedback loop (102).

The fluid density meter (100) may include the switch (140) to switch between selecting a resonance frequency and maintaining the resonance frequency. The switch (140) may break the feedback loop (102) and apply a different signal to the test fixture (110) during startup of the fluid density meter (100).

Figure 3:
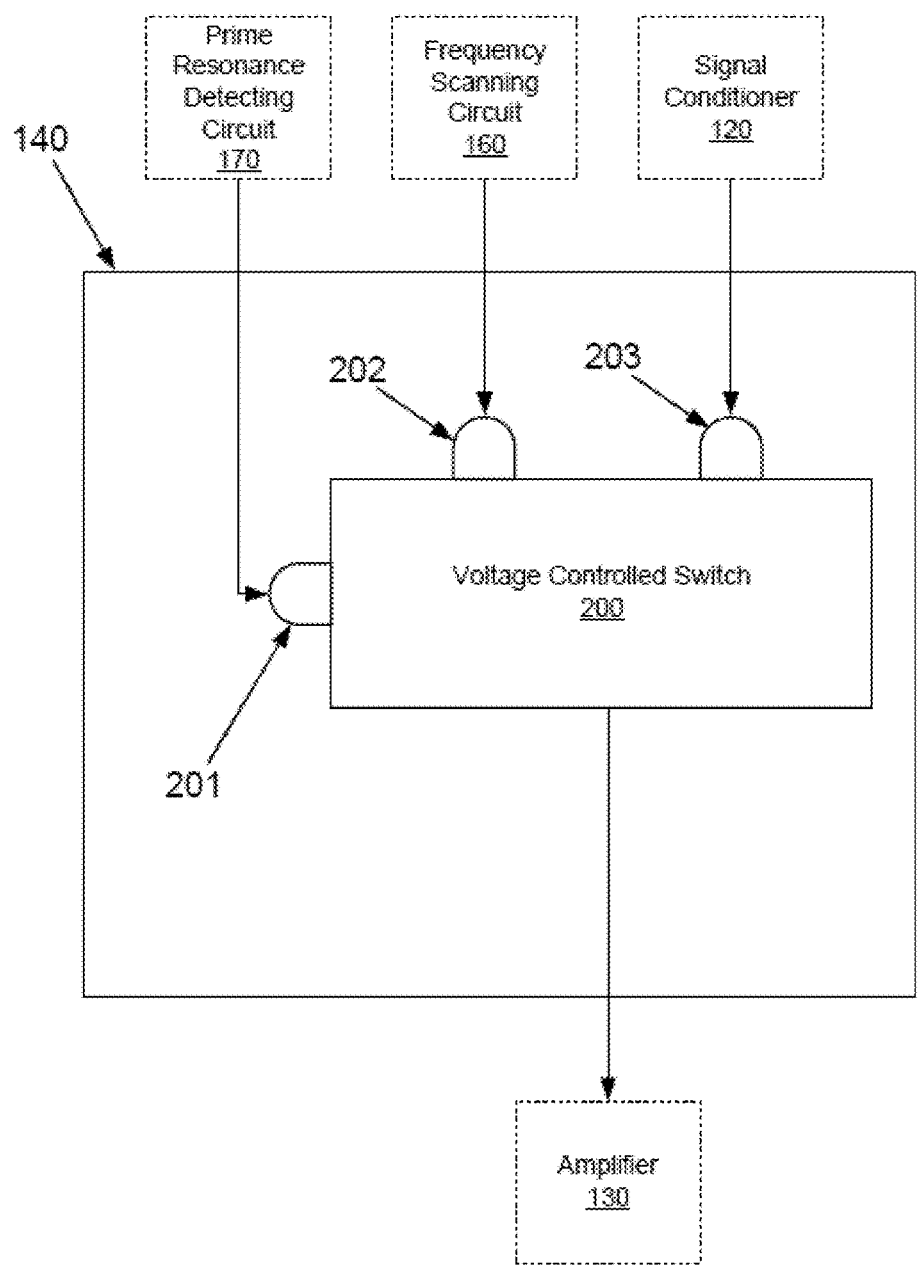
FIG. 3 shows a diagram of a switch in accordance with one or more embodiments of the disclosure.

FIG. 3 shows a diagram of a switch (140) in accordance with one or more embodiments of the disclosure. Signals sent from other circuits or components are indicated by arrows from or to the associated circuit or component with a dashed border. Specifically, the diagram of the switch (140) shows connections between the switch (140) and other parts of the fluid density meter (100). The switch (140) may switch the signal sent to the amplifier (130) between a signal sent from the frequency scanning circuit (160) and the signal sent from the signal conditioner (120). The switch (140) receives a signal from the prime resonance detecting circuit (170) that determines which signal is sent to the amplifier (130).

The switch (140) may include a voltage controlled switch (200). In one or more embodiments of the disclosure, the voltage controller switch (200) may be implemented as a circuit on a printed circuit board including discrete components as is known in the art or as a single discrete circuit element. The voltage controlled switch may include a first switchable input (202), a second switchable input (203), and a control input (201). The voltage controlled switch (200) may output either the signal received on the first switchable input (202) or the signal received on the second switchable input (203) based on the signal received on the control input (201). For example, the voltage controlled switch (200) may receive a 0 V signal on the control input (201) and output the signal received from the frequency scanning circuit (160) on the first switchable input (202). In another example, the voltage controlled switch (200) may receive a 5 V signal on the control input (201) and output the signal received from the signal conditioner (120) on the second switchable input (203).

With reference to FIG. 2, the startup circuit (101) further includes a startup trigger (150). The startup trigger (150) may send a trigger signal to the frequency scanning circuit (160) in response to a measurement initiation. In one or more embodiments of the disclosure, the measurement initiation may be powering up the fluid density meter (100). In one or more embodiments of the disclosure, the measurement initiation may be a pressing of a button or other form of receivable input as would be known to one of ordinary skill in the art, e.g. a signal sent via a network, a signal sent by a wireless link, a signal sent by another electronic component such as a computer, etc. The startup trigger (150) may be implemented as a circuit as would be known to one of ordinary skill in the art.

With further reference to FIG. 2, the startup circuit (101) further includes a frequency scanning circuit (160). The frequency scanning circuit (160) may generate a time varying voltage and sweep the frequency of the time varying voltage over a range.

Figure 4:
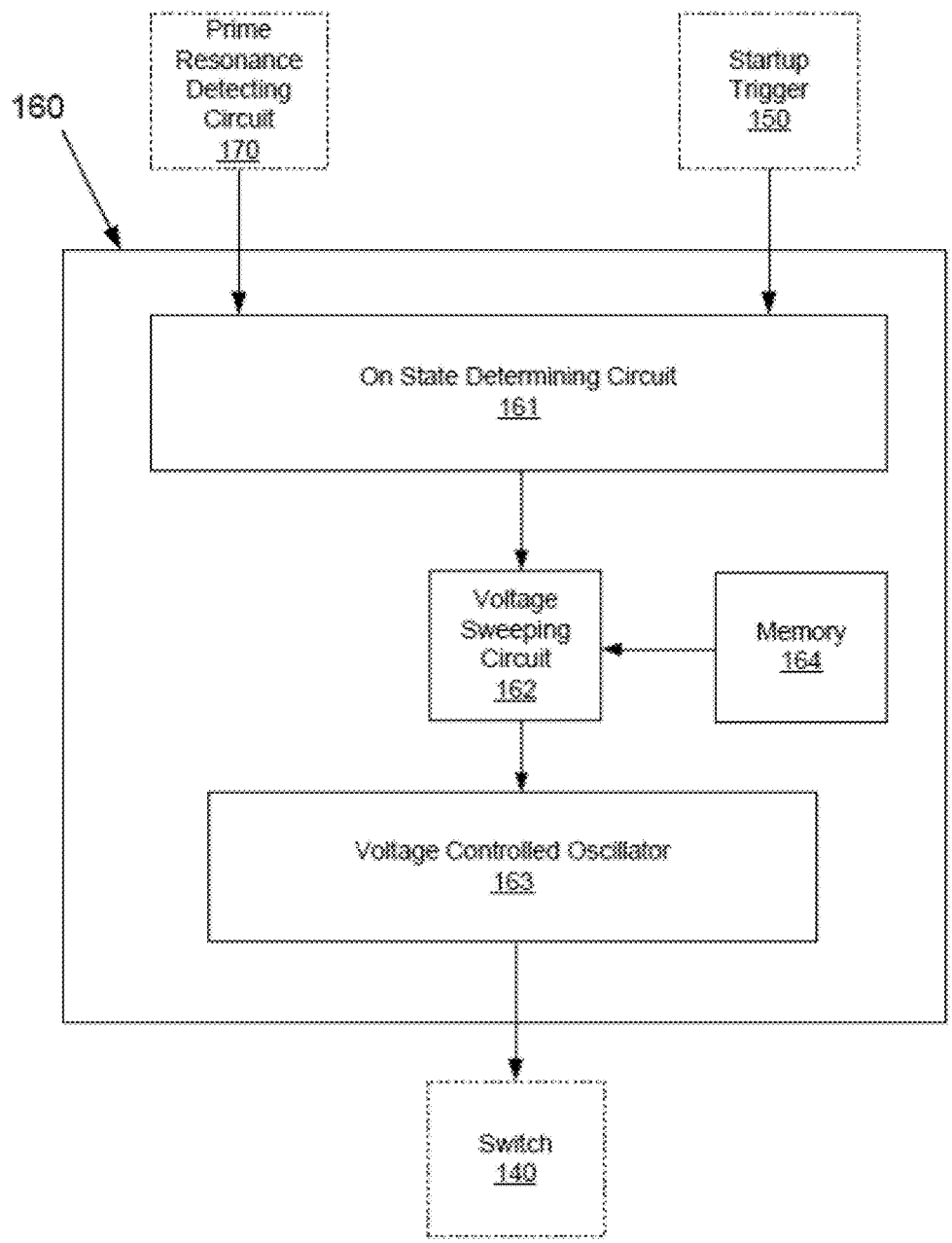
FIG. 4 shows a diagram of a frequency scanning circuit in accordance with one or more embodiments of the disclosure.

FIG. 4 shows a frequency scanning circuit (160) in accordance with one or more embodiments of the disclosure. Signals sent from other circuits or components are indicated by arrows from or to the associated circuit or component with a dashed border. The frequency scanning circuit (160) may include an on state determining circuit (161), a voltage sweeping circuit (162), and a voltage controlled oscillator (163). The aforementioned circuits may be implemented as analog circuits, digital circuits including instructions stored on a non-transitory computer readable medium, digital signal processing units, or any other type of circuit as would be known to one of ordinary skill in the art. The on state determining circuit (161) may receive a signal from the startup trigger (150) and the prime resonance detecting circuit (170). The on state determining circuit (161) turns the frequency scanning circuit (160) on or off based on the received signals. For example, if the startup trigger (150) sends a signal indicating a measurement has not been triggered, the on state determining circuit (161) shuts the frequency scanning circuit (160) off. In another example, if the startup trigger (150) sends a signal indicating a measurement trigger has been received, then the on state determining circuit (161) evaluates the signal received from the prime resonance detecting circuit (170). If the prime resonance detecting circuit (170) indicates that a prime resonance has not been detected, the on state determining circuit (161) turns the frequency scanning circuit (160) on.

The voltage controlled oscillator (163) may generate a voltage at a frequency proportional to an applied voltage. The generated voltage may be output as a signal to the switch (140). The voltage controlled oscillator (163) receives input from a voltage sweeping circuit (162). The voltage sweeping circuit (162) generates a sweeping voltage and sweeps the magnitude of the sweeping voltage over a range and at a rate of change of the sweeping voltage. For example, the sweeping voltage may be swept from 0V to 5V at a rate of 1 V/s. By sweeping the magnitude of the sweeping voltage, the frequency of the output voltage of the frequency scanning circuit (160) varies over a range corresponding to the range of the magnitude of the sweeping voltage swept by the voltage sweeping circuit (162). The frequency scanning circuit (160) may also include a memory (164) that stores the range of the magnitude of the swept voltage of the voltage sweeping circuit (162) and the rate of change of the sweeping voltage. The range and rate stored in memory may be based on the test fixture (110).

With reference to FIG. 2, the fluid density meter (100) may also include a prime resonance detecting circuit (170). The prime resonance detecting circuit (170) may determine a prime resonance frequency of the resonance frequencies vibrations supported by the test fixture (110) based on an output voltage of the test fixture (110). As seen in FIG. 2, the test fixture (110) may output a voltage to the signal conditioner (120). The signal conditioner (120) conditions the signal, as previously noted, and then sends a portion of the signal to the resonance detecting circuit (170). When the prime resonance detecting circuit (170) detects a prime resonance frequency, the prime resonance detecting circuit (170) may send a signal to the frequency scanning circuit (160) that turns the frequency scanning circuit (160) off and may send a second signal to the switch (140) that indicates the feedback circuit should be closed, e.g. the prime resonance detecting circuit (170) may send a signal instructing the voltage controlled switch (200, FIG. 3) to output the signal received from the signal conditioner (120) to the amplifier (130).

Figure 5:
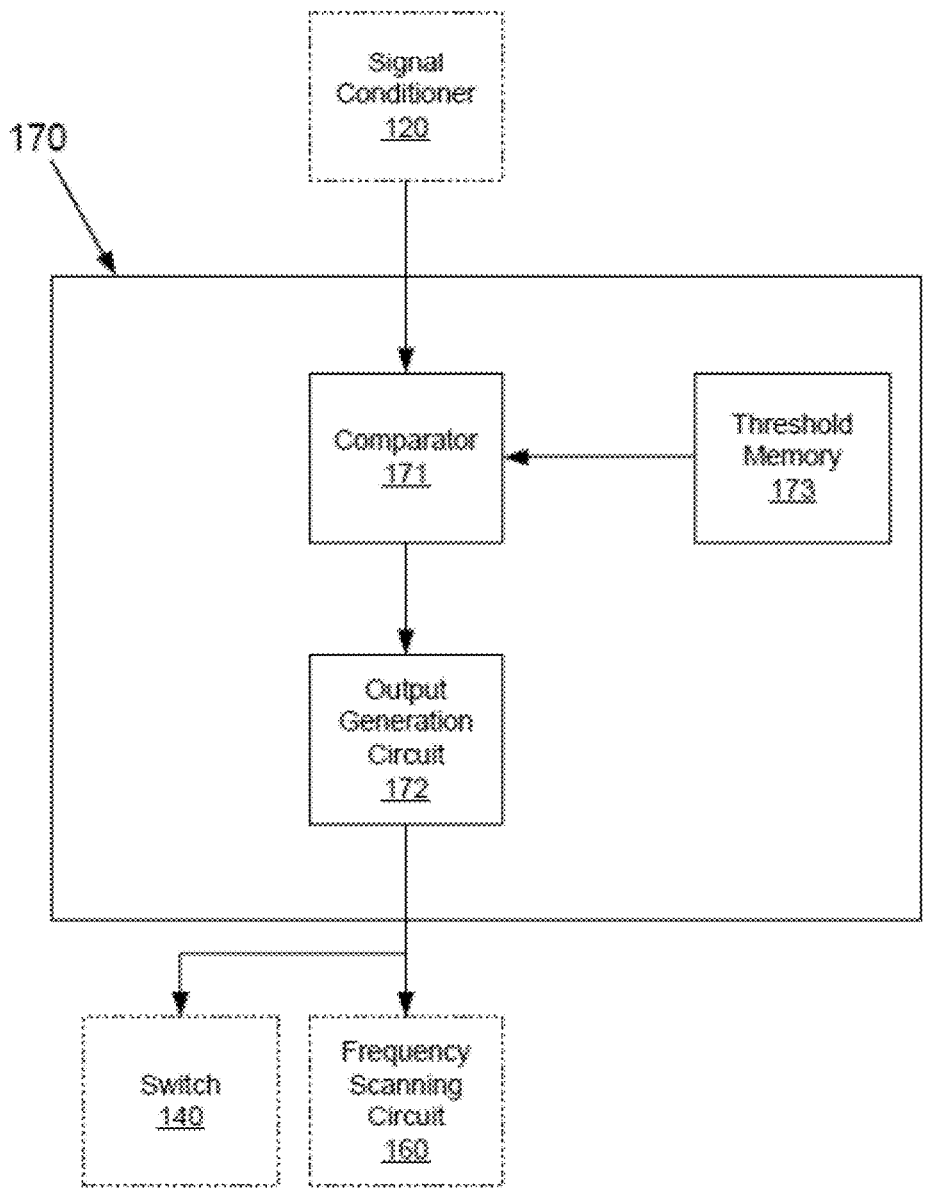
FIG. 5 shows a diagram of a prime resonance detecting circuit in accordance with one or more embodiments of the disclosure.

FIG. 5 shows a prime resonance detecting circuit (170) in accordance with one or more embodiments of the disclosure. Signals sent from other circuits or components are indicated by arrows from or to the associated circuit or component with a dashed border. The prime resonance detecting circuit (170) may be implemented as an analog circuit, digital circuit including instructions stored on a non-transitory computer readable medium, digital signal processing unit, or any other type of circuit as would be known to one of ordinary skill in the art. The prime resonance detecting circuit (170) may include a comparator (171), an output generator (172), and a threshold memory (173). The comparator (171) may compare the magnitude of the voltage signal received from the signal conditioner (120) to a threshold stored in the threshold memory (173). If the magnitude of the received signal exceeds the threshold value, the comparator may determine that a prime resonance frequency is present. In response to a fact that a prime resonance frequency is present, the comparator (171) may send a signal to the output generation circuit (172).

The output generation circuit (172) may generate a signal that indicates a prime resonance has been detected in response to receiving the detection signal from the comparator (171). The signal, indicates a prime resonance frequency has been detected, may be sent to the switch (140) and the frequency scanning circuit (160). As described above, the frequency scanning circuit (160) may turn off in response to receiving the signal indicating a prime resonance frequency has been detected and the switch (140) may switch the output of the voltage controlled switch (200) to the signal received from the signal conditioner (120) in response to receiving the signal indicating a prime resonance frequency has been detected.

Figure 6:
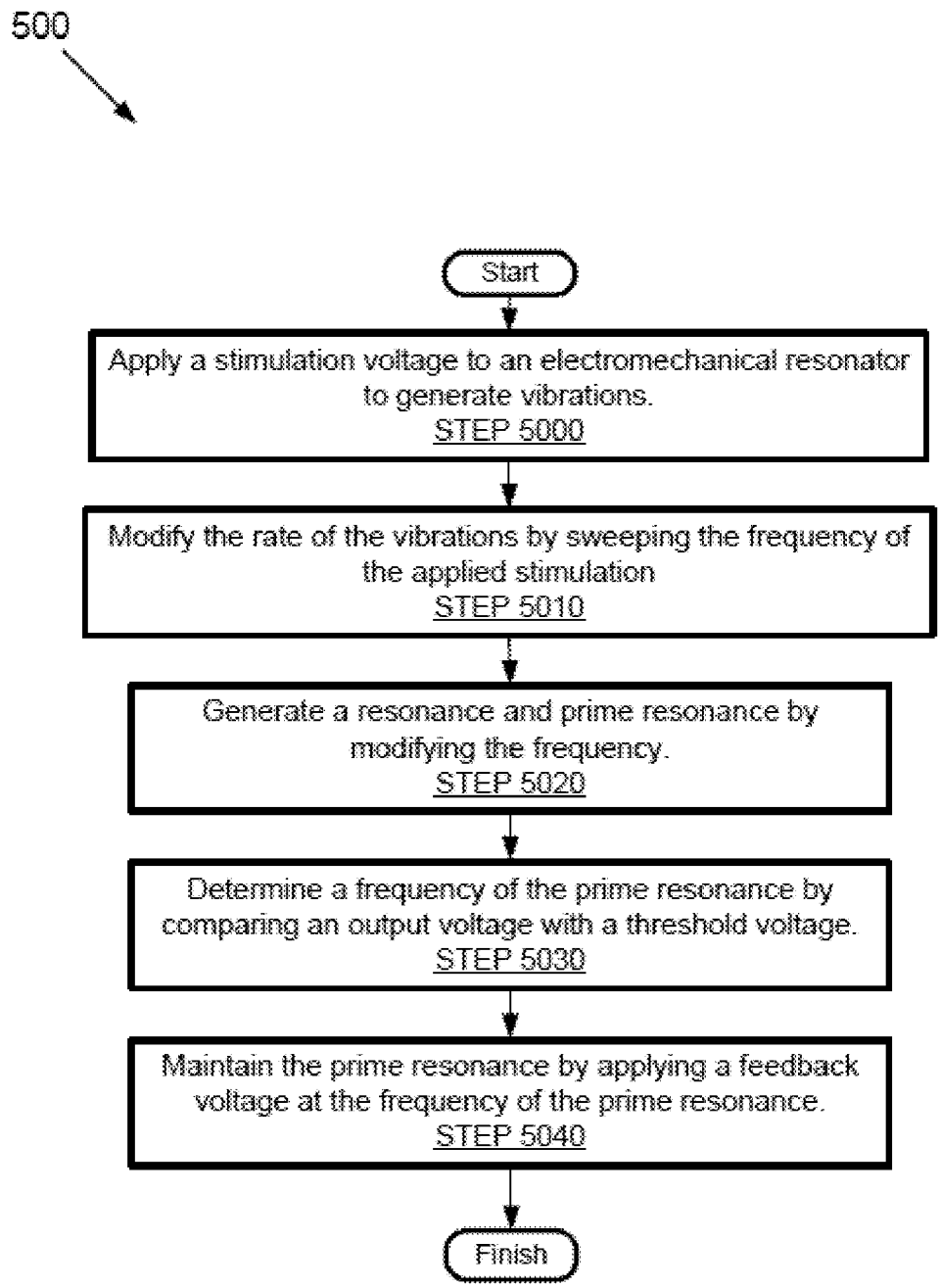
FIG. 6 shows a flow chart of a method of measuring a fluid density in accordance with one or more embodiments of the disclosure.

FIG. 6 shows a flowchart (500) according to one or more embodiments of the disclosure. The method depicted in FIG. 6 may be used to measure the density of a fluid in accordance with one or more embodiments of the disclosure. One or more steps shown in FIG. 6 may be omitted, repeated, and/or performed in a different order among different embodiments.

At Step 5000, a stimulation voltage is applied to a test fixture. Applying the voltage to the test fixture may generate vibrations. With reference to FIG. 2, the frequency scanning circuit (160) may generate a time varying voltage at a first frequency. The time varying voltage may be sent to the test fixture (110), via the switch (140) and amplifier (130). In response to the applied time varying voltage, the amplifier (130) and the test fixture (110) may generate vibrations at an amplitude corresponding to the first frequency. For example, the test fixture (110) may include a transducer, e.g. a piezoelectric transducer or a magnetic loop transducer that generates vibrations in response to an applied voltage.

At Step 5010, an amplitude of the vibrations generated by the test fixture in response to the applied voltage is modified by sweeping the frequency of the applied stimulation. With reference to FIG. 2, the frequency scanning circuit (160) may sweep the first frequency of the generated time varying voltage from the voltage sweeping circuit (162). In one or more embodiments of the disclosure, the first frequency may be swept over a range stored in a memory of the frequency scanning circuit (160) range. The range may be based on the test fixture (110). By changing the frequency of the time varying voltage generated by the frequency scanning circuit (160) and applied as a stimulation voltage to the test fixture (110), a transducer of the test fixture (110) may produce vibrations at a frequency corresponding to the sweeping frequency. For example, if a frequency of the generated voltage is varied from 1 kHz to 5 kHz, vibrations at a frequency of 1 kHz to 5 kHz may be produced by the transducer. The rate of change of the frequency of the time varying voltage generated by the frequency scanning (160) may also be stored in a memory of the frequency scanning circuit (160). For example, the memory may include a rate of change of 100 Hz/second, e.g. an initial frequency may be 1 kHz and at 2 seconds the frequency would be 1.2 kHz.

At Step 5020, a resonance frequency and a prime resonance frequency are generated by the test fixture (110) by modifying the frequency of the stimulation voltage. With reference to FIG. 2, the test fixture (110) may support multiple resonance frequencies as described above. By sweeping the frequency of the stimulation voltage, vibrations at rates corresponding to each resonance frequency are applied to the test fixture. In response to each resonance frequency, the test fixture may generate an output voltage proportional to the mode order, e.g. a smaller voltage as the mode order increases.

At Step 5030, a prime resonance frequency is determined by comparing an output voltage with a threshold voltage. With reference to FIG. 2, output voltages may be transmitted to the prime resonance detecting circuit (170). The prime resonance detecting circuit (170) may compare the received voltages to threshold levels stored in a threshold memory (173, FIG. 5). When a magnitude of the received voltages exceeds the magnitude stored in memory, the prime resonance detecting circuit (170) determines the prime resonance frequency as identified.

At Step 5040, the prime resonance frequency is maintained by applying a feedback voltage at the prime resonance frequency. As noted above, when the prime resonance detecting circuit (170, FIG. 2) detects a prime resonance frequency, the prime resonance detecting circuit may send a signal to the switch (140, FIG. 2) and frequency scanning circuit (160, FIG. 2) indicating a prime resonance frequency has been detected. In response to the signal, the switch (140, FIG. 2) switches the output of the switch to the signal received from the signal conditioner (120, FIG. 2). By switching the signal, the feedback loop (102) is closed and causes an existing resonance frequency vibration to be maintained in the test fixture (110). By switching at the time of detecting the prime resonance frequency, the resonance frequency vibration of the test fixture (110) is maintained as the prime resonance frequency.

Thus, the method shown in FIG. 6 enables a prime resonance frequency, among a number of supported resonance frequencies, to be applied to a test fixture. By enabling application of a prime resonance frequency, embodiments of the disclosure may prevent error in the determination of a fluid density due to the application of a higher order mode of vibration to a test fixture, e.g. application of a non-prime resonance frequency. Fluid density measurements in accordance with embodiments of the disclosure may avoid the error by preventing the application of a non-prime resonance frequency to a test fixture.

EXAMPLE

Figure 7:
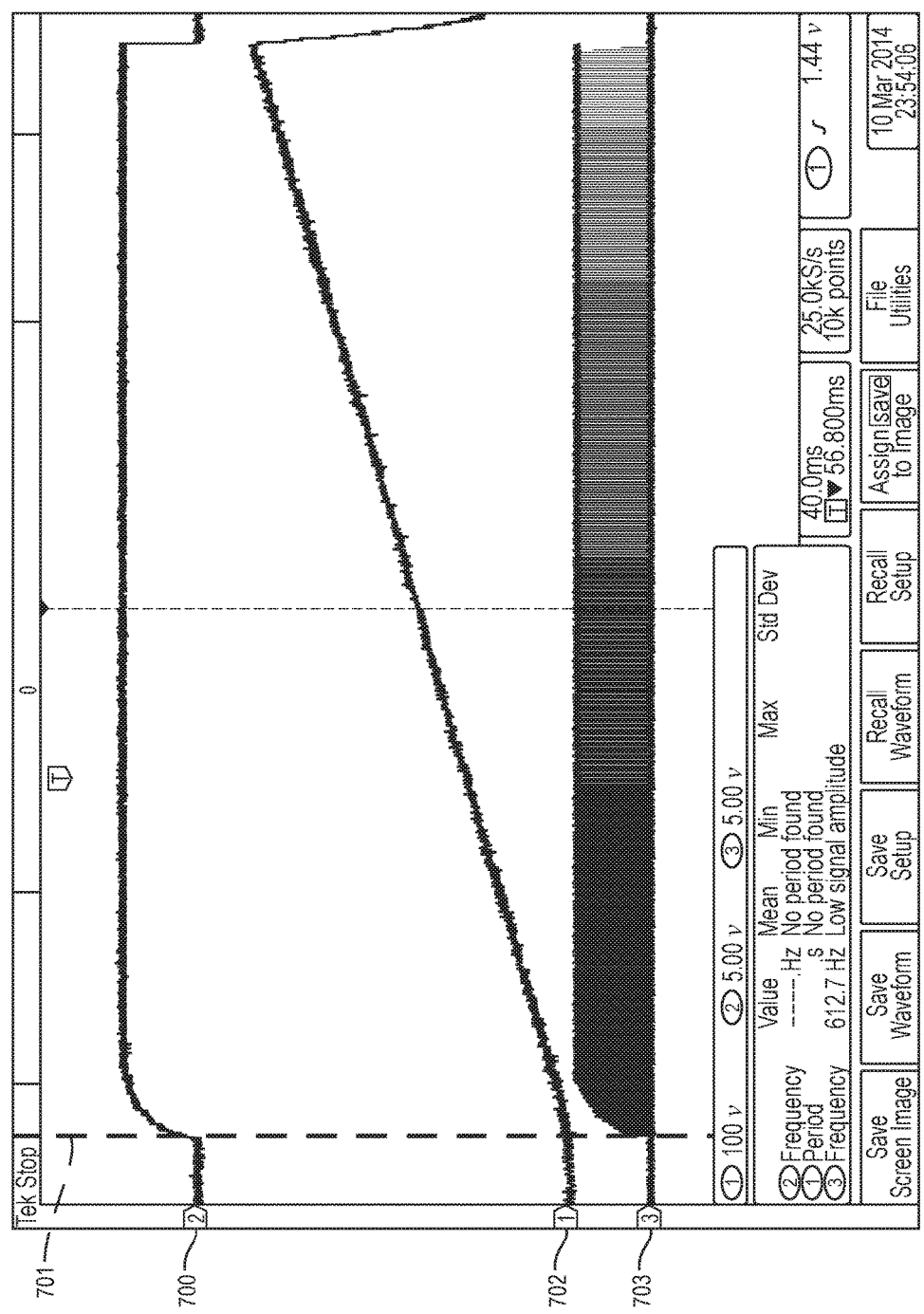
FIG. 7 shows measured voltages of a fluid density meter in accordance with one or more embodiments of the disclosure.
Figure 8:
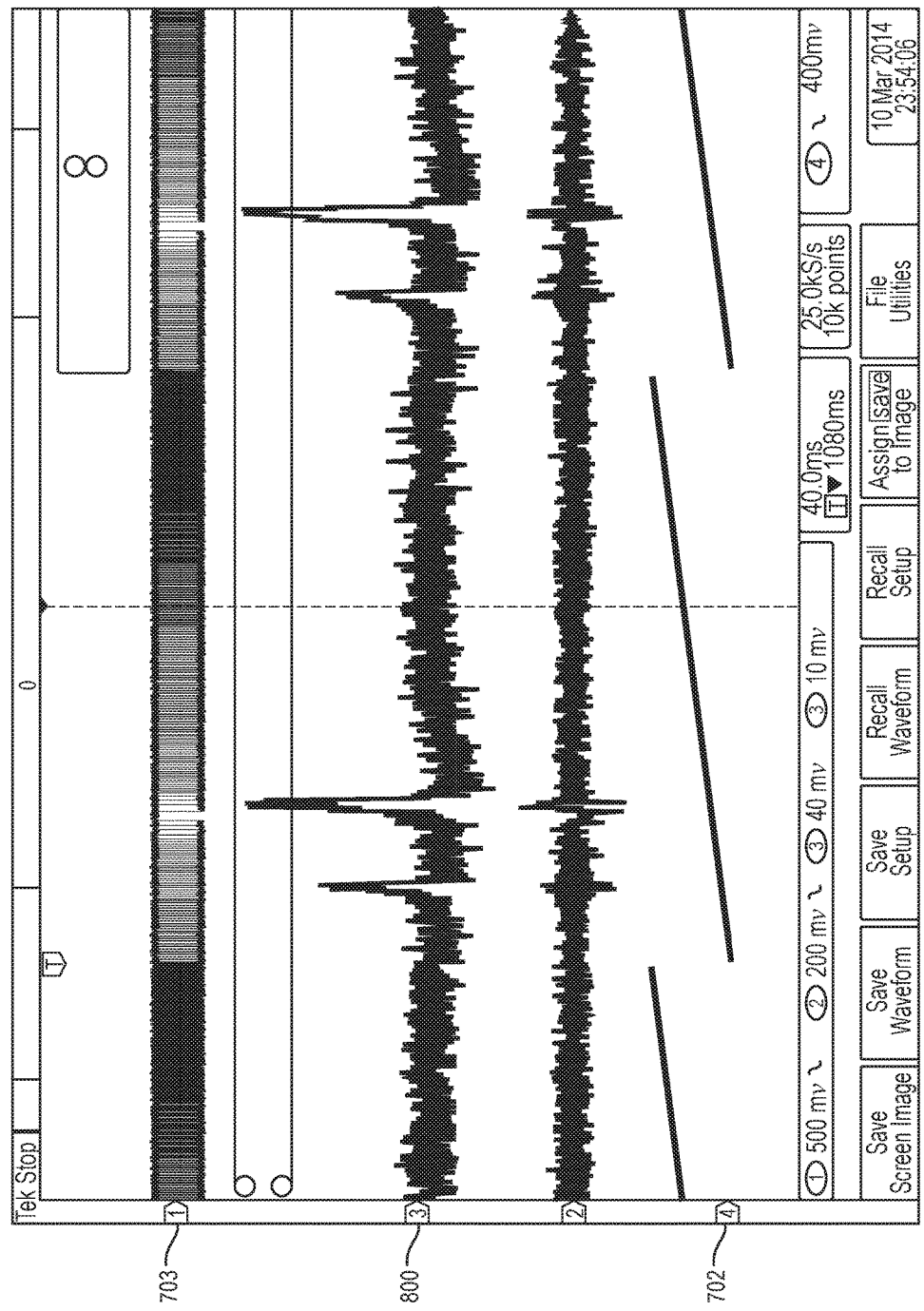
FIG. 8 shows measured voltages of a fluid density meter in accordance with one or more embodiments of the disclosure.
Figure 9:
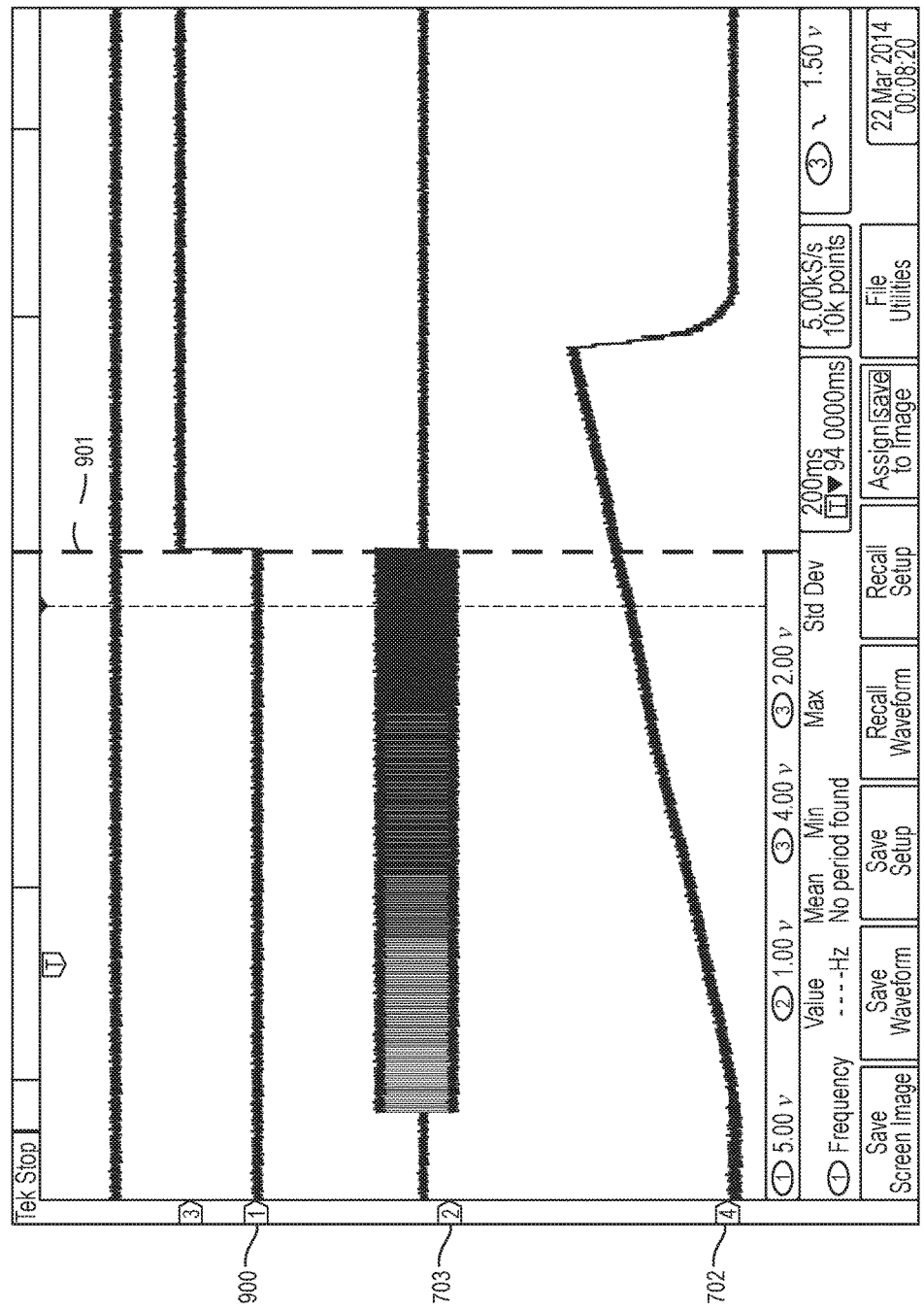
FIG. 9 shows measured voltages of a fluid density meter in accordance with one or more embodiments of the disclosure.

FIGS. 7-9 show measured voltages vs. time for a fluid density meter in accordance with one or more embodiments of the disclosure. Specifically, FIGS. 7-9 show voltages and frequencies of the fluid density meter measured by an oscilloscope.

With reference to FIG. 7, the first trace (700) indicates the output voltage generated by the trigger startup (150, FIG. 2) in response to receiving a measurement start signal. More specifically, the trigger startup (150, FIG. 2) generates an output voltage at a first time (701) indicated by the dashed line. In response to receiving the output voltage generated by the trigger startup (150, FIG. 2), the on state determining circuit (161, FIG. 4) determined the state as on and activates the voltage sweeping circuit (162, FIG. 4). In response to being activated, the voltage sweeping circuit (162, FIG. 4) generated a ramping voltage (702). As seen from FIG. 7, the ramping voltage (702) ramps from a small value (0 V) to a large value (5 V) over a period of time. However, the ramping voltage (702) may ramp from another range such as a range from (0 V)-(12 V) or from a large voltage to a small voltage or in other ways without departing from the scope of the disclosure.

The voltage controller oscillator (163, FIG. 4) receives the ramping voltage (702) and generates a corresponding sweeping frequency voltage signal (703) having a frequency that corresponds to the magnitude of the ramping voltage (702). Thus, as the magnitude of the ramping voltage (702) changes, the frequency of the sweeping voltage signal (703) also changes. The sweeping frequency of the voltage signal (703) shown in FIG. 7 is at a high frequency and thus appears as a blurred horizontal bar.

With reference to FIGS. 7 and 8, the sweeping frequency voltage signal (703) is received by the test fixture (110, FIG. 2). The test fixture (110, FIG. 2) generates an output voltage (800). As seen from FIG. 8, the test fixture (110, FIG. 2) may generate voltages corresponding to resonance frequencies. The two spikes in the output voltage (800) correspond to resonance frequencies. As seen from the output voltage (800) the magnitude of the resonances is different and thus a primary resonance frequency may be determined based on the magnitude of the output spikes.

With reference to FIGS. 8 and 9, the output voltage (800, FIG. 8) of the test fixture (110, FIG. 2) is received by the prime resonance detecting circuit (170, FIG. 5). The prime resonance detecting circuit (170, FIG. 5) compares the output voltage (800) to a threshold voltage value. If the output voltage (800, FIG. 8) exceeds the threshold voltage value, the prime resonance detecting circuit (170, FIG. 5) generates an output voltage (900). The frequency scanning circuit (160, FIG. 2) terminates the sweeping voltage (703) in response to the output voltage (900) generated by the prime resonance detecting circuit (170, FIG. 5). In FIG. 9, the output voltage (900) is indicated as a change in the magnitude of the output voltage (900) and the terminated voltage signal with sweeping frequency (703) is indicated as the blurred horizontal bar reducing to a line at a time (901) when the output voltage (800, FIG. 8) of the test fixture (110, FIG. 2) exceeds the threshold level. The switch (140, FIG. 3) disconnects the startup circuit (101, FIG. 2) and closes the feedback loop (102, FIG. 2) in response to the output voltage (900) generated by the prime resonance detecting circuit (170, FIG. 5).

While the invention has been described above with respect to a limited number of embodiments, those skilled in the art, having the benefit of this disclosure, will appreciate that other embodiments can be devised which do not depart from the scope of the invention as disclosed herein. Accordingly, the scope of the invention should be limited only by the attached claims.

What is claimed is:

1. A fluid density meter, comprising:
   a voltage sweeping circuit configured to generate a voltage that increases from a small value to a larger value over a period of time;
   a voltage controlled oscillator configured to receive the voltage and generate a frequency voltage signal that corresponds to a magnitude of the voltage value;
   a test fixture configured to generate vibrations, comprising:
   a vibration source configured to generate vibrations in response to the frequency voltage signal wherein the vibrations comprise a prime resonance frequency and a second resonance frequency over the period of time,
   an interior region configured to hold a test fluid and transmit the vibrations to the test fluid;
   a pickup circuit configured to generate an output voltage that corresponds to the prime resonance frequency and the second resonance frequency over the period of time; and
   a prime resonance detecting circuit configured to detect the prime resonance frequency from the output voltage.

2. The fluid density meter according to claim 1, wherein the prime resonance detecting circuit is configured to detect the prime resonance by comparing a magnitude of the output voltage to a threshold value and send a prime resonance detected signal to a frequency scanning circuit in response to detecting the prime resonance.

3. The fluid density meter according to claim 2, wherein the threshold value is based on the prime resonance frequency.

4. The fluid density meter according to claim 2, wherein the frequency scanning circuit is configured to terminate the voltage from the voltage sweeping circuit in response to receiving the prime resonance detected signal.

5. The fluid density meter according to claim 4, further comprising:
   a feedback loop configured to:
   generate, in response to the frequency scanning circuit terminating the voltage from the voltage sweeping circuit, a feedback voltage comprising the prime resonance frequency, and
   supply the feedback voltage to the vibration source as the frequency voltage signal.

6. The fluid density meter according to claim 5, further comprising:
   a switch configured to:
   connect a voltage input of the test fixture that receives the frequency voltage signal to an alternating voltage output on the frequency scanning circuit, connect the voltage input of the test fixture that receives the frequency voltage signal to the feedback voltage output on the feedback loop,
wherein the alternating voltage output and the feedback voltage output are not connected to the voltage input of the test fixture at the same time.

7. The fluid density meter according to claim 1, wherein the test fixture is configured to support the prime resonance frequency and the second resonance frequency wherein the prime resonance frequency corresponds to a first magnitude of the output voltage and the second resonance frequency corresponds to a second magnitude of the output voltage.

8. The fluid density meter according to claim 1, further comprising a startup trigger configured to activate the voltage sweeping circuit in response to a fluid test initiation.

9. A method of initiating a fluid density measurement, comprising:
   generating a stimulation voltage that increases from a small value to a larger value over a period of time;
   receiving the stimulation voltage and generating a frequency voltage signal corresponding to a magnitude of the voltage value;
   generating vibrations in a test fixture in response to the frequency voltage signal, wherein the vibrations comprise a prime resonance frequency and a second resonance frequency over the period of time;
   transmitting the vibrations to a test fluid;
   generating an output voltage that corresponds to the vibration frequency; and
   detecting the prime resonance from the output voltage.

10. The method according to claim 9, further comprising:
   terminating the stimulation voltage in response to detecting the prime resonance frequency.

11. The method according to claim 9, wherein a rate of change over the period of time of the frequency voltage signal is proportional to a frequency of the vibrations.

12. The method according to claim 9, wherein the prime resonance frequency and the second resonance frequency over the period of time are based on a structure of the test fixture.

13. The method according to claim 9, further comprising applying a feedback voltage, based on the detected prime resonance frequency, to a test fixture wherein a frequency of the feedback voltage corresponds to the prime resonance frequency.

14. The method according to claim 9, to detect the prime resonance frequency further comprising:
   comparing a magnitude of the output voltage to a threshold value; and
   sending the prime resonance detected signal to the frequency scanning circuit in response to detecting the prime resonance frequency.

* * * * *